US009132065B2

(12) United States Patent
Evert et al.

(10) Patent No.: US 9,132,065 B2
(45) Date of Patent: Sep. 15, 2015

(54) ENTERAL FEEDING PERCUTANEOUS ACCESS CLIP

(71) Applicant: Cook Medical Technologies LLC, Bloomington, IN (US)

(72) Inventors: Kathryn R. Evert, Bloomington, IN (US); Kurt J. Tekulve, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 175 days.

(21) Appl. No.: 13/862,535

(22) Filed: Apr. 15, 2013

(65) Prior Publication Data

US 2013/0289486 A1 Oct. 31, 2013

Related U.S. Application Data

(60) Provisional application No. 61/640,188, filed on Apr. 30, 2012.

(51) Int. Cl.
*A61M 5/32* (2006.01)
*A61J 15/00* (2006.01)

(52) U.S. Cl.
CPC .......... *A61J 15/0046* (2013.01); *A61J 15/0061* (2013.01)

(58) Field of Classification Search
CPC ................. A61B 17/3415; A61B 2017/00349; A61J 15/0015; A61J 15/0069; A61J 15/0023; A61J 15/0019; A61J 15/007; A61M 2025/0233
USPC .................................................. 604/910, 174
See application file for complete search history.

(56) References Cited

U.S. PATENT DOCUMENTS

| | | | | |
|---|---|---|---|---|
| 4,886,500 | A | 12/1989 | Lazarus | |
| 5,257,975 | A | 11/1993 | Foshee | |
| 6,546,280 | B2 | 4/2003 | Osborne | |
| 6,669,708 | B1 | 12/2003 | Nissenbaum et al. | |
| 7,452,347 | B2 | 11/2008 | DeLegge | |
| 7,621,903 | B2 | 11/2009 | DeLegge | |
| 7,857,789 | B2 | 12/2010 | Bettuchi et al. | |
| 7,942,862 | B2 | 5/2011 | Hart et al. | |
| 2005/0215959 | A1* | 9/2005 | Whitington | 604/278 |
| 2010/0113880 | A1 | 5/2010 | Page | |
| 2012/0130184 | A1 | 5/2012 | Richard | |

FOREIGN PATENT DOCUMENTS

| | | | |
|---|---|---|---|
| WO | WO 2007/019117 | A1 | 2/2007 |
| WO | WO 2011/072100 | A2 | 6/2011 |

* cited by examiner

*Primary Examiner* — Rebecca E Eisenberg
(74) *Attorney, Agent, or Firm* — Woodard, Emhardt, Moriarty, McNett & Henry LLP

(57) ABSTRACT

Devices for securing open a stoma in the abdomen of a patient are disclosed. Additionally, devices that secure a percutaneously-implanted tube are disclosed. In one embodiment, a helically would wire forms a first coil arrangement inside of the stomach cavity of a patient and a second coil arrangement outside of the body of the patient, the first coil arrangement and second coil arrangement cooperating to squeeze the stomach wall and the abdominal wall into an adjacent position. Methods and other embodiments are disclosed.

20 Claims, 10 Drawing Sheets

ENTERAL FEEDING PERCUTANEOUS ACCESS CLIP

CROSS-REFERENCE TO RELATED APPLICATIONS

This application claims the benefit of U.S. Provisional Application No. 61/640,188, filed Apr. 30, 2012, which is hereby incorporated by reference in its entirety.

TECHNICAL FIELD

The present disclosure pertains generally to medical devices and methods of securing an open stoma and/or securing a percutaneously-implanted tube.

BACKGROUND

An ostomy placement is a surgical procedure that creates an opening in the body. For example, gastrostomy, jejunostomy, colostomy, and ileostomy are procedures that create openings that can be used for the placement of feeding or drainage tubes. Feeding tubes are often used for patients that have impaired swallowing ability. Drainage tubes are used for removing materials, such as bodily waste, from inside the body of the patient.

The percutaneous placement of a tube through the abdominal wall of the patient, such as in a gastrostomy procedure, can be performed to treat temporary and/or permanent conditions, such as chronic disabilities. With reference to gastrostomy and gastrojejunostomy procedures as a particular example, catheters for use in these procedures are inserted directly through the abdominal wall of the patient and into the stomach. Gastrostomy catheters can then be used for feeding the patient directly into the stomach, wherein nourishing substances are inserted into an external opening in the catheter and are transported by the catheter to the interior of the patient's stomach. With the gastrojejunostomy catheter, the distal portion of the catheter inside the patient is long enough to be positioned in the jejunum, such that feeding can bypass the stomach entirely.

Because these catheters are left in place for extended periods of time, and because they extend externally from the patient, there is a need for some retention means for preventing the catheter from being accidentally removed from the patient. Additionally, since these catheters are often intentionally removed for the clearing of blockages from the within the tube and/or to allow the patient to have a more active lifestyle and improved comfort, there is a need for means to allow the removal and insertion of the catheter without having to regain access to the internal organ. Thus, there is a need for improvement in this field.

SUMMARY

In certain aspects, the present disclosure provides devices and methods for securing access to a location within the body of a patient. In accordance with some forms of the present disclosure, a securing device is used to secure a stoma in an open position, permitting access to a location within the body. Additionally, some forms of the present disclosure use a securing device to secure a tube in a stoma. In some embodiments, a device for securing the wall of an organ to the abdominal wall of a patient comprises a device body having a distal portion, a proximal portion, and a central portion extending between said distal portion and said proximal portion; the device body configurable between an insertable configuration and an expanded configuration; the distal portion comprising a first elongate body that in the expanded configuration forms a first coil arrangement having a first maximum outer dimension; the proximal portion comprising a second elongate body that in the expanded configuration forms a second coil arrangement having a second maximum outer dimension; and the central portion forming a central portion arrangement having a third maximum outer dimension; wherein the first and the second maximum outer dimensions are greater than the third maximum outer dimension; and wherein the first coil arrangement is self-expanding. Additionally, in some instances, the device body is configured to have the first coil arrangement and the second coil arrangement cooperate to bring a wall of an organ into close proximity with the abdominal wall of a patient. In some embodiments the device body is longitudinally extendable in the expanded configuration, and, in some embodiments, the central portion arrangement defines a tissue-free lumen when implanted in the body of a patient.

In some instances, the present disclosure provides a kit comprising a device for securing a percutaneously-implantable tube, having a device body having a distal portion, a proximal portion, and a central portion extending between said distal portion and said proximal portion; the device body configurable between an insertable configuration and an expanded configuration; the distal portion comprising a first elongate body that in the expanded configuration forms a first coil arrangement having a first maximum outer dimension; the proximal portion comprising a second elongate body that in the expanded configuration forms a second coil arrangement having a second maximum outer dimension; and the central portion forming a central portion arrangement having a third maximum outer dimension; wherein the first and the second maximum outer dimensions are greater than the third maximum outer dimension; and wherein the proximal portion and the distal portion in the expanded configuration are effective to squeeze the wall of an organ and the abdominal wall of a patient into an adjacent position; and a percutaneously-implantable tube arranged to fit within the central portion and access a location within a body of a patient. The first elongate body and the second elongate body can be portions of an elongate member. The device can also comprise a biomaterial cover positioned over the central portion. It is also envisioned that the kit can include a bag, a delivery device, a needle, and/or a dilator.

In some embodiments, the present disclosure teaches a device for securing the wall of an organ to the abdominal wall of a patient, comprising a wire having a distal portion, a proximal portion, and a central portion extending between said distal portion and said proximal portion; the wire configurable between an insertable configuration and an expanded configuration; the distal portion comprising a first securing portion that in the expanded configuration forms a first coil arrangement having a first maximum outer dimension; the proximal portion comprising a second securing portion that in the expanded configuration forms a second coil arrangement having a second maximum outer dimension; and the central portion forming a third coil arrangement having a third maximum outer dimension; wherein the first and the second maximum outer dimensions are greater than the third maximum outer dimension.

Further forms, objects, features, aspects, benefits, advantages, and embodiments of the present disclosure will become apparent from a detailed description and drawings provided herewith.

DESCRIPTION OF THE SELECTED EMBODIMENTS

Figure 1:
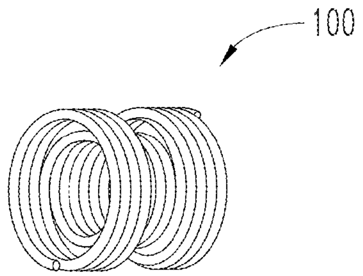
FIG. 1 illustrates a perspective view of one embodiment of a securing device.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

With respect to the specification and claims, it should be noted that the singular forms "a", "an", "the", and the like include plural referents unless expressly discussed otherwise. As an illustration, references to "a device" or "the device" include one or more of such devices and equivalents thereof. It also should be noted that directional terms, such as "up", "down", "top", "bottom", and the like, are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

The reference numerals in the following description have been organized to aid the reader in quickly identifying the drawings where various components are first shown. In particular, the drawing in which an element first appears is typically indicated by the left-most digit(s) in the corresponding reference number. For example, an element identified by a "100" series reference numeral will likely first appear in FIG. 1, an element identified by a "200" series reference numeral will likely first appear in FIG. 2, and so on.

The following specification describes the use of devices and methods in the areas of gastsrostomy and gastrojejunostomy and cecostomy. While the present disclosure finds particular use in these fields, those skilled in the art will recognize that the devices and methods disclosed herein may be used in any application where connection from the outside of the patient's body to an internal cavity within the body is desired, such as in the biliary tree, the liver, the kidney, etc.

Figure 2:
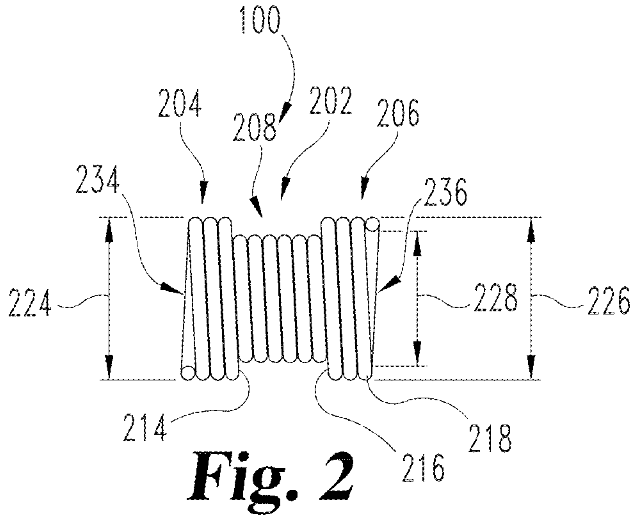
FIG. 2 illustrates a plan view of one embodiment of a securing device.
Figure 3:
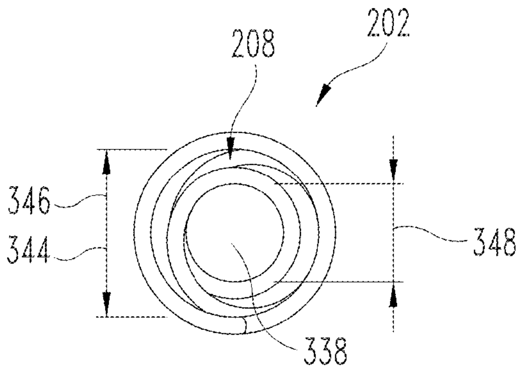
FIG. 3 illustrates an end view of one embodiment of a securing device.

FIGS. 1, 2, and 3 illustrate one embodiment of a securing device 100. The securing device 100 can comprise a device body 202 that is configurable between an insertable configuration and an expanded configuration. The device body 202 in the insertable configuration can be arranged for containment by a delivery device and advancement into a location in the body of a patient. In an expanded configuration, the device body 202 can be arranged to secure portions of tissue of the body into an adjacent arrangement and/or secure an access opening to a location within the body.

The device body 202 in an expanded configuration can comprise a distal portion 204, a proximal portion 206, and a central portion 208 extending between the distal portion 204 and the proximal portion 206. The distal portion 204 can be arranged for positioning within a void of the body, with the central portion 208 arranged to extend through a tissue wall of the body from the distal portion 204 towards the proximal portion 206, arranged to be positioned outside of the body. Additionally, in some embodiments, the distal portion 204 and/or the proximal portion 206 have/has portions arranged to contact a tissue wall of the body. For example, the distal portion 204 can have a distal tissue surface 214 arranged to contact a tissue wall, and the proximal portion 206 can have a proximal tissue surface 216 arranged to contact a tissue wall.

Portions of the securing device 100 can be formed from an elongate member 218, such as a wire. In some instances the elongate member 218 forms a coil arrangement in one or more portions of the device body 202, such as the distal portion 204, the proximal portion 206, and/or the central portion 208. For example, an elongate member 218 can be coiled into a helically wound arrangement to form the distal portion 204, proximal portion 206, and central portion 208. In some instances, the device body 202 resembles a spring having opposite ends of greater diameter than a central portion.

The device body 202 in an expanded configuration can have a distal portion 204 with a maximum outer dimension 224, a proximal portion 206 with a maximum outer dimension 226, and a central portion 208 with a maximum outer dimension 228. In some instances, the maximum outer dimension 224 of the distal portion 204 and/or the maximum outer dimension 226 of the proximal portion 206 are/is greater than the maximum outer dimension 228 of the central portion 208.

The distal portion 204 can define a distal lumen 234 having a distal lumen dimension 344, and proximal portion 206 can define a proximal lumen 236 having a proximal lumen dimension 346. Additionally, the central portion 208 can define a central lumen 338 having a central lumen dimension 348.

Figure 4:
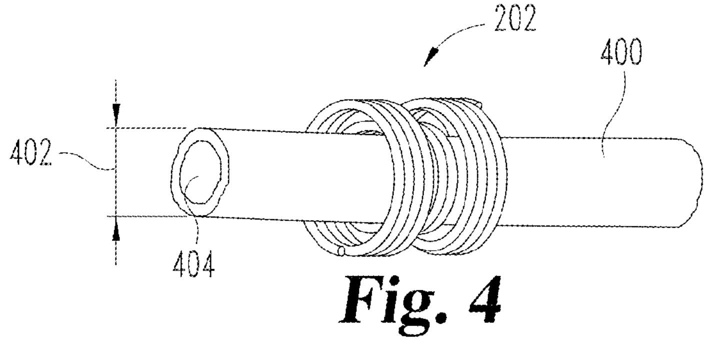
FIG. 4 illustrates a perspective view of one embodiment of a securing device, positioned over a tube.
Figure 5:
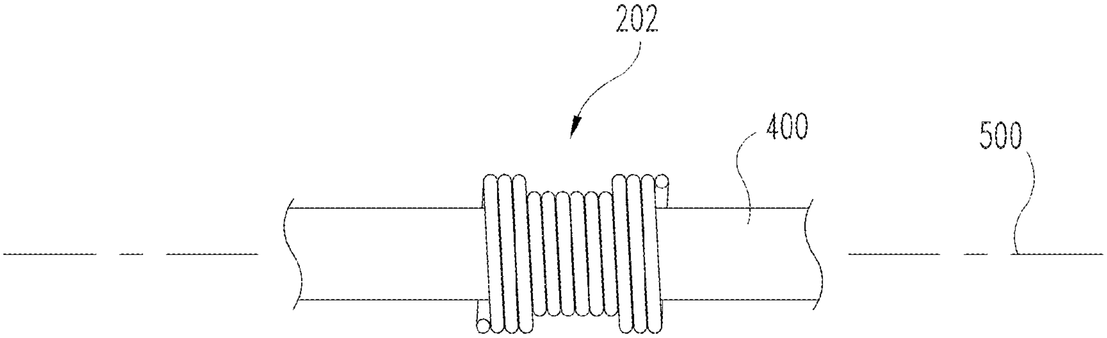
FIG. 5 illustrates a plan view of one embodiment of a securing device, positioned over a tube.
Figure 6:
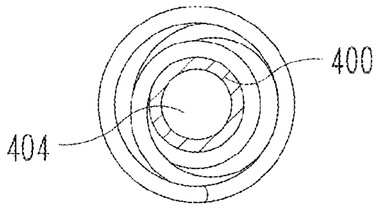
FIG. 6 illustrates an end view of one embodiment of a securing device, positioned over a tube.

As illustrated in FIGS. 4, 5, and 6, a portion of the securing device 100 can be arranged to retain a tube 400. For example, the central lumen 338, the distal lumen 234, and/or the proximal lumen 236 may be arranged to retain a tube 400. In some embodiments, a portion of the securing device 100 can be arranged to resist movement of the tube 400 in a direction along a longitudinal axis 500 of the securing device 100. Alternatively and/or additionally a portion of securing device 100 can be arranged to resist movement of the tube 400 direction orthogonal to the longitudinal axis 500.

To resist movement of the tube 400 in a direction along the longitudinal axis 500, the distal lumen dimension 344, proximal lumen dimension 346, and/or central lumen dimension 348 can be substantially the same size as the maximum outer dimension 402 of the tube 400. For example, the central lumen dimension 348 of a central portion 208 may be substantially the same size as the maximum outer dimension 402 of the tube 400 so that a portion of the central portion 208 contacts a surface of the tube 400 and frictionally resists movement of the tube 400 in a direction along the longitudinal axis 500. Alternatively, the distal lumen dimension 344, proximal lumen dimension 346 and/or central lumen dimension 348 can be smaller than the maximum outer dimension 402 of the tube 400 so as to cause an interference fit, sometimes referred to as a "friction fit". For example, the central lumen dimension 348 of the central portion 208 may be smaller than the maximum outer dimension 402 of the tube 400.

Figure 7:
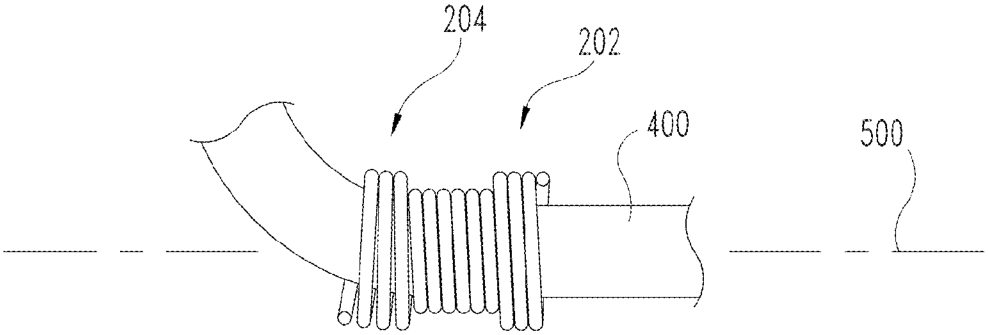
FIG. 7 illustrates a plan view of one embodiment of a securing device, positioned over a tube and having a deflectable portion being deflected by the tube.

In some embodiments, the distal portion 204 and/or the proximal portion 206 of the device body 202 can have a deflectable portion arranged to resist movement of the tube 400 in a direction towards a tissue wall and/or orthogonal to the longitudinal axis 500. For example, as illustrated in FIG. 7, the distal portion 204 may have a deflectable portion that is arranged to delimit deflection of the tube 400. In some instances, the distal portion 204 may have portions that expand and/or contract when the tube 400 deflects towards a tissue wall. In these embodiments, the deflected arrangement of the distal portion 204, such as the expanded and/or contracted portions, may apply a force to the tube 400 to deflect the tube 400 away from the tissue wall.

Figure 8:
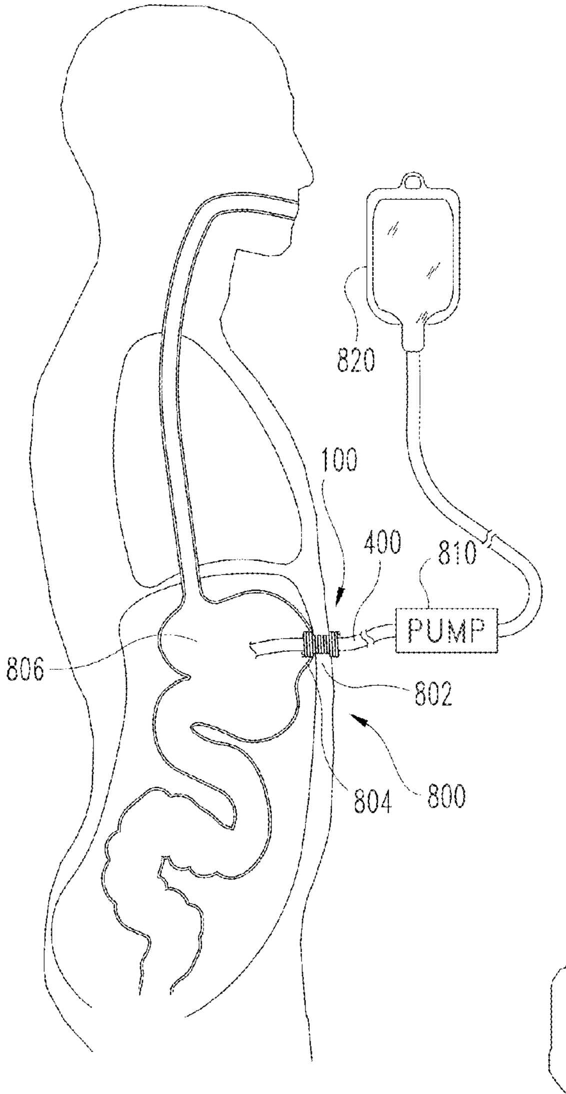
FIG. 8 illustrates one embodiment of a securing device retaining a tube implanted in the body of a patient.
Figure 9:
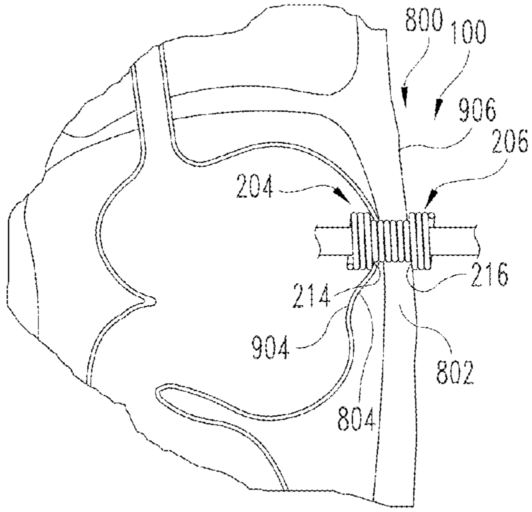
FIG. 9 illustrates one embodiment of a securing device retaining a tube implanted in the body of a patient.
Figure 10:
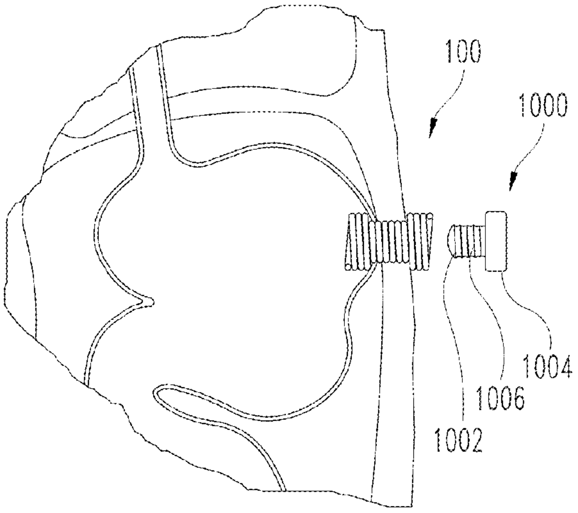
FIG. 10 illustrates one embodiment of a securing device and a plug.

The tube 400 can have an inner lumen 404 arranged to transport a fluid into and/or out of a portion of the body of a patient. As illustrated in FIGS. 8, 9, and 10, the securing device 100 can be positioned within the abdomen 800 of a patient. In some embodiments, the securing device 100 extends through the abdominal wall 802, the stomach wall 804, and into the stomach cavity 806. Additionally, the securing device 100 can be arranged to provide access for and/or secure a tube 400, such as a percutaneous feeding tube.

The tube 400 can be attached to a pump 810, such as a peristaltic pump, and/or a bag 820, such as a feeding bag. In some instances, the pump 810 can be used to pump fluid from the bag 820 into the stomach cavity 806 through the tube 400 retained by the securing device 100. In other instances, the pump 810 can be used to pump fluid from the stomach cavity 806 through the tube 400 to a bag 820.

The securing device 100 can have portions that cooperate to bring the abdominal wall 802 and the stomach wall 804 into close proximity. For example, a coil arrangement of the distal portion 204 and a coil arrangement of the proximal portion 206 may cooperate to bring the abdominal wall 802 and the stomach wall 804 into close proximity. In some embodiments, the distal tissue surface 214 of the distal portion 204 contacts an inner surface 904 of the stomach wall 804 and the proximal tissue surface 216 of the proximal portion 206 contacts a surface 906, e.g., the skin, of the abdominal wall 802.

In some instances, the distal portion 204, proximal portion 206, and/or central portion 208 of the device body 202 can be effective to squeeze the wall of an organ, such as the stomach wall 804, and the abdominal wall 802 of a patient into an adjacent position. For example, the central portion 208 of the device body 202 may have a resiliently extendable portion arranged to force the distal portion 204 and the proximal portion 206 towards the central portion 208 and one-another when the central portion 208 is extended.

As illustrated in FIGS. 9 and 10, portions of the securing device 100 can reside in various locations within the body of a patient. For instance, the distal portion 204 of the device body 202 can reside within the stomach cavity 806 defined by the stomach wall 804. The central portion 208 of the device body 202 can reside in the stomach wall 804 and/or the abdominal wall 802, and the proximal portion 206 of the device body can reside outside out of the abdominal wall 802 and/or on the outside surface of the abdomen 800 of the patient.

As illustrated in FIG. 10, some embodiments of the securing device 100 continue to maintain an open stoma with a cavity of an organ without the tube 400. For example, the central lumen 338 of the central portion 208 of the device body 202 can define a tissue-free lumen. Additionally, the central lumen 338 can communicate with the distal lumen 234 and the proximal lumen 236 so as to permit access through the proximal portion 206, central portion 208, and distal portion 204 of the device body 202 into the stomach cavity 806. This may permit easily insertion, removal, and/or exchange of the tube 400.

The securing device 100 can also be arranged to receive a plug 1000 when a tube 400 is not retained in the proximal lumen 236 and/or central lumen 338. For example, the central lumen 238 of the device body 202 can be arranged to receive a first portion 1002 of the plug 1000 and/or the proximal lumen 236 can be arranged to receive a second portion 1004 of the plug 1000.

In some embodiments, the securing device 100 is arranged to receive a threaded portion 1006 of the plug 1000. For example, the central portion 208 of the device body 202 may have a threaded portion arranged to engage a threaded portion 1006 on the first portion 1002 of the plug 1000. When the threaded portion of the central portion 208 and the threaded portion 1006 of the plug 1000 are engaged, the plug 1000 is secured within the central lumen 338 of the device body 202.

Figure 11:
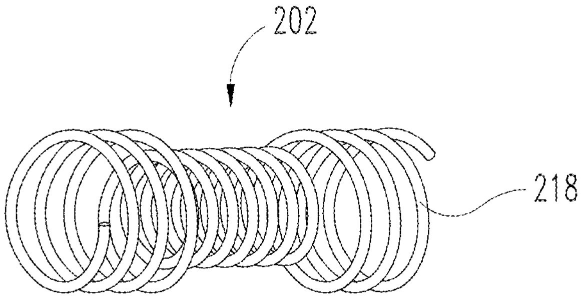
FIG. 11 illustrates a perspective view of one embodiment of a securing device in a longitudinally extendable arrangement.

The securing device 100 may be longitudinally extendable in the expanded configuration. As illustrated in FIG. 11, the distal portion 204, proximal portion 206, and/or central portion 208 of the device body 202 may be extended (e.g., stretched) along the longitudinal axis 500 of the securing device 100. In some instances, the central portion 208 of the device body 202 is longitudinally extended when the device body 202 is used to press two tissue wall portions towards one another. In these instances, the central portion 208 may resemble a spring, and, for example, apply a force to the tissue walls proportional to the distance that the central portion 208 is longitudinally extended.

Various embodiments of the securing device 100 may have coiled portions with coils that are not in abutting contact when the device body 202 is in its expanded configuration. For instance, the arrangement of the coils of the device body 202 may resemble those illustrated in FIG. 11. The coils are longitudinally spaced along the longitudinal axis 500 of the securing device 100.

Figure 12:
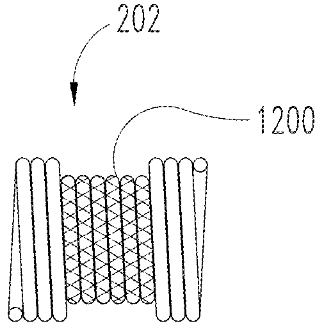
FIG. 12 illustrates a plan view of one embodiment of a securing device.
Figure 13:
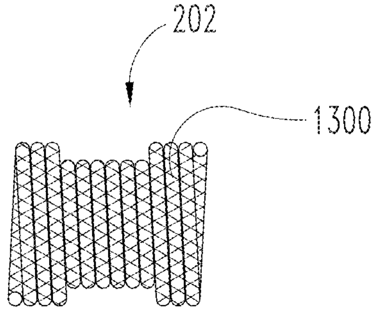
FIG. 13 illustrates a plan view of one embodiment of a securing device.

As illustrated in FIGS. 12 and 13, portions of the securing device 100 may have a covering and/or a coating. In some embodiments, the securing device 100 can include a covering 1200 extending over one or more of the portions of the device body 202. The covering can be made of any material apparent to one of ordinary skill in the art to be suitable. For example, a covering 1200 may comprise a biomaterial such as an extracellular matrix material (e.g., porcine small intestinal submucosa). In some instances, the covering 1200 comprises Teflon and/or a woven polyester fabric or an expanded polytetrafluoroethylene (ePTFE). The covering 1200 can be attached to the distal portion 204, proximal portion 206, and/or the central portion 208 of the device body.

In some embodiments, the securing device 100 may have a coating 1300 on the device body 202. The coating can include a regenerative material, such as cells, to heal the wound created by the stoma and/or to reduce infection. Additionally, in some instances, the coating 1300 may be applied on top of the covering 1200.

Figure 14:
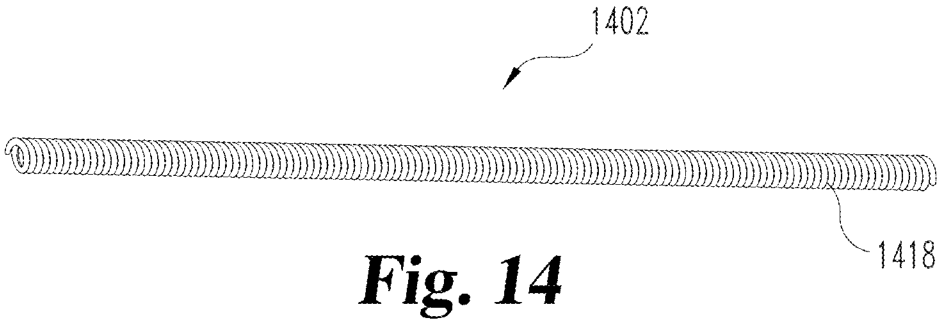
FIG. 14 illustrates a perspective view of one embodiment of an elongate member.
Figure 15:
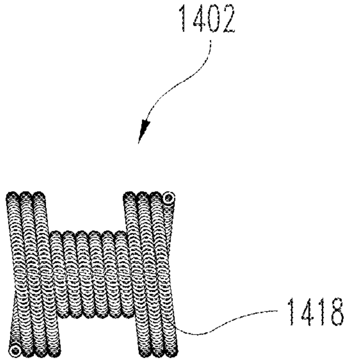
FIG. 15 illustrates a plan view of one embodiment of a securing device having the elongate member illustrated in FIG. 14.

Various combinations and modifications may be made to the disclosed embodiments. For example, as illustrated in FIGS. 14 and 15, the device body 1402 may comprise an elongate member 1418, the elongate member 1418 formed by a helically wound member similar to a piano string. FIG. 14 illustrates one embodiment of the device body 1402 comprising the elongate member 1418 in an insertable configuration. FIG. 15 illustrates one embodiment of the device body 1402 in an expanded configuration.

Figure 16:
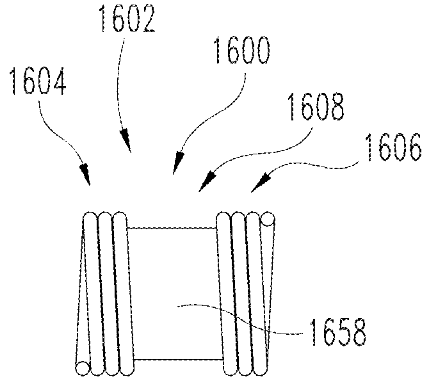
FIG. 16 illustrates a plan view of one embodiment of a securing device.

FIG. 16 illustrates another embodiment of a securing device 1600 comprised of a device body 1602 having a distal portion 1604, a proximal portion 1606, and a central portion 1608. In this illustration, the distal portion 1604 and the proximal portion 1606 of the device body 1602 are formed from one or more helically wound (e.g., coiled) elongate members. The central portion 1608 can be formed without coils. For example, the central portion 1608 may comprise a sleeve 1658 extending between the distal portion 1604 and the proximal portion 1606 of the device body. The sleeve 1658 may be made of any biocompatible material known by one of ordinary skill in the art. For example, the sleeve may be a woven polyester fabric or an expanded polytetrafluoroethylene (ePTFE), just to name a few non-limiting examples.

Delivery Devices and Methods

FIGS. 17, 18, 19, 20, and 21 illustrate a device and a method that may be used for implanting the securing device, such as the securing device 100. Prior to and/or during insertion of the securing device 100 into the body of the patient, the device body 202 of the securing device 100 can be in the insertable configuration and retained by a delivery device 1700. In some instances, the device body 202 can be positioned within a delivery device 1700 and/or a portion thereof, such as a needle 1702. The needle 1702 can be advanced to penetrate the abdominal wall 802 and the wall of an organ within the body of the patient, such as the stomach wall 804.

Figure 17:
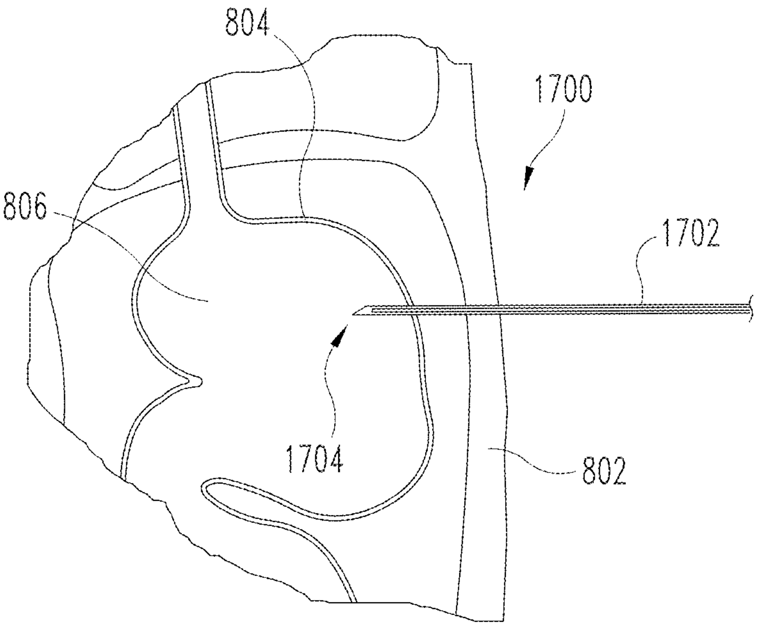
FIGS. 17, 18, 19, 20, and 21 illustrate an embodiment device and an embodiment method that can be used to implant a securing device.
Figure 18:
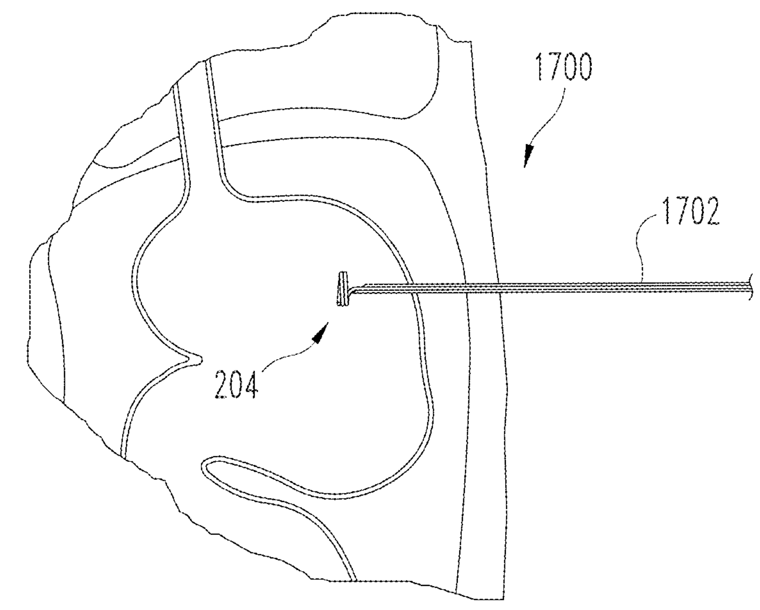
Figure 19:
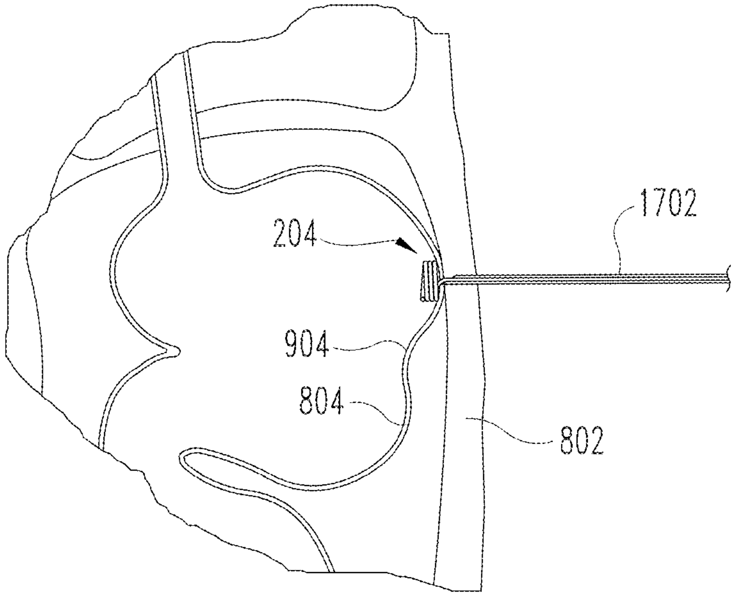
Figure 20:
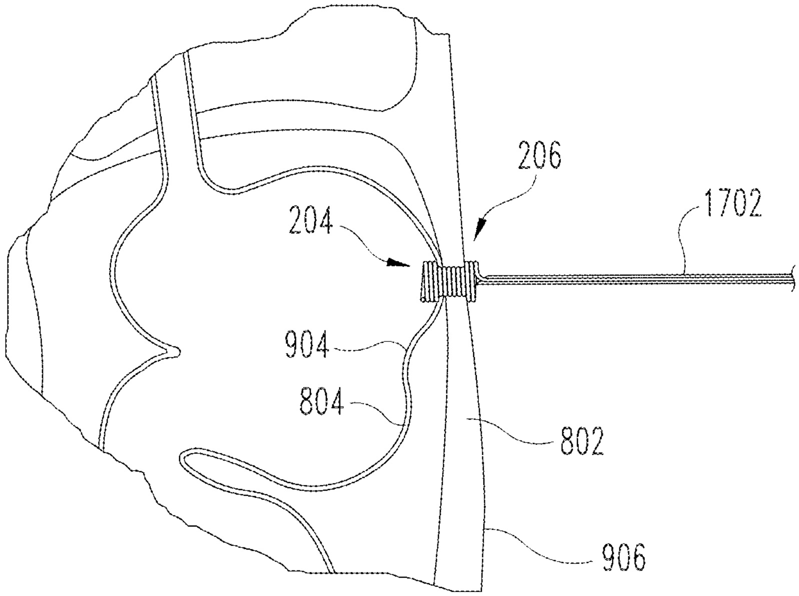
Figure 21:
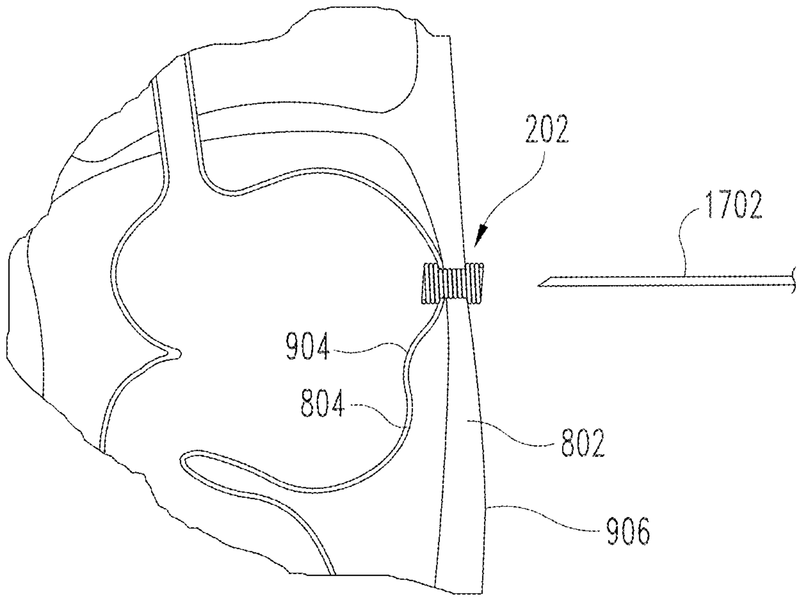
Figure 22:
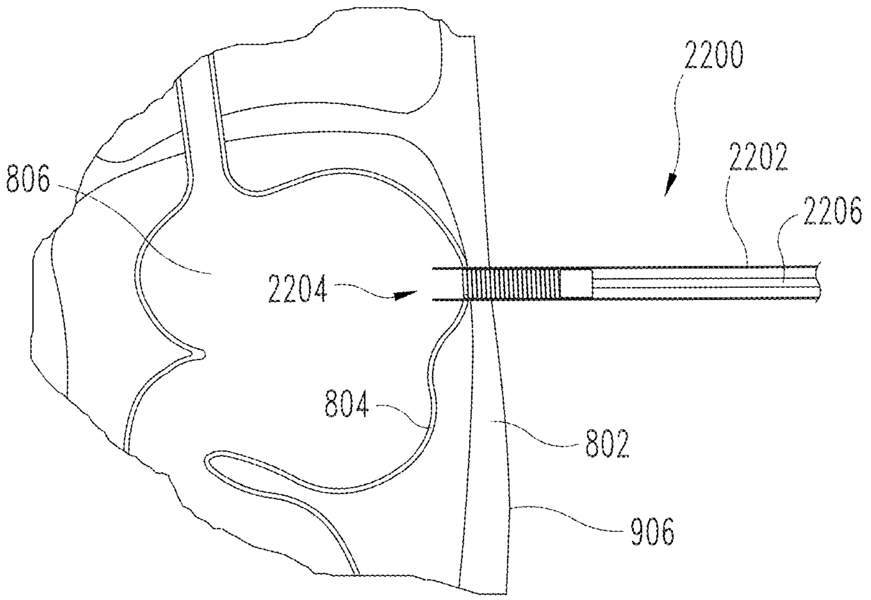
FIGS. 22, 23, 24, and 25 illustrate an embodiment device and an embodiment method that can be used to implant a securing device.
Figure 23:
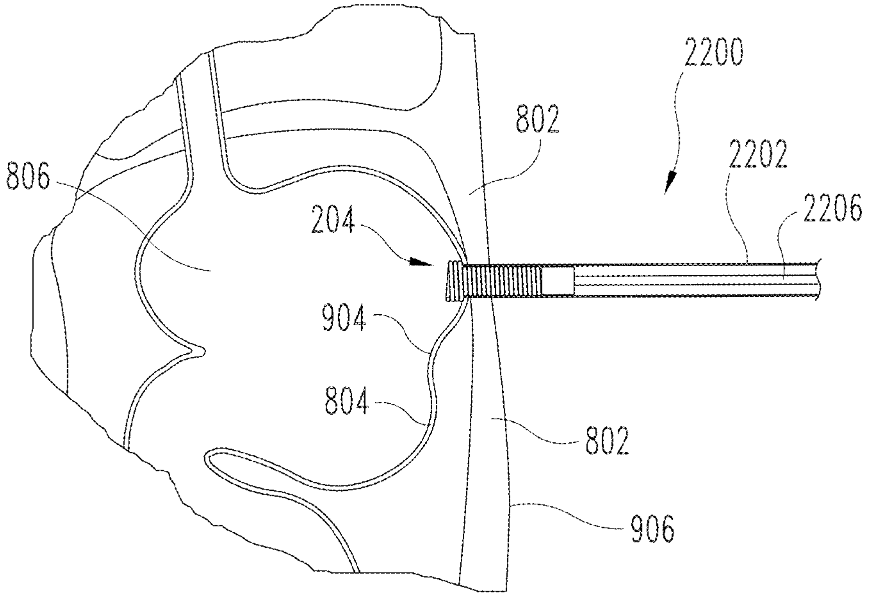
Figure 24:
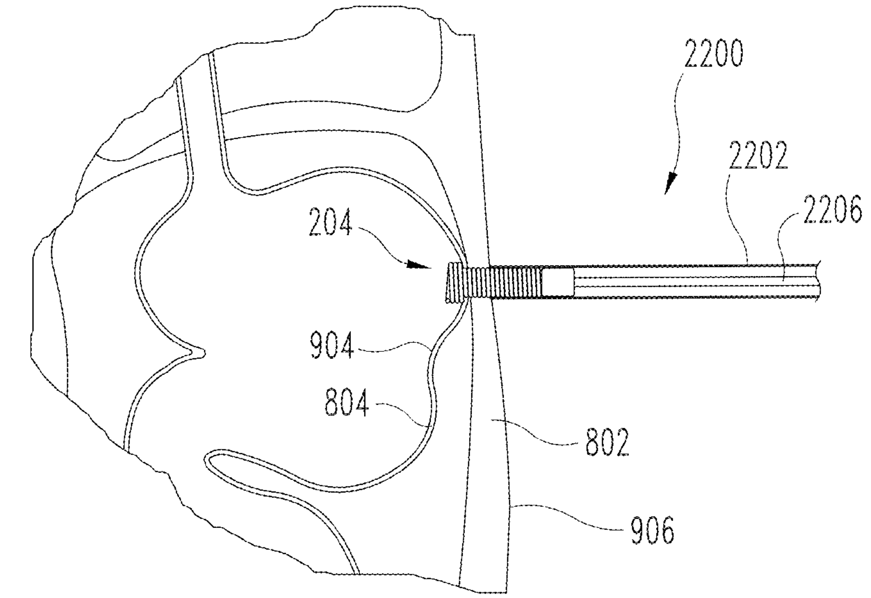
Figure 25:
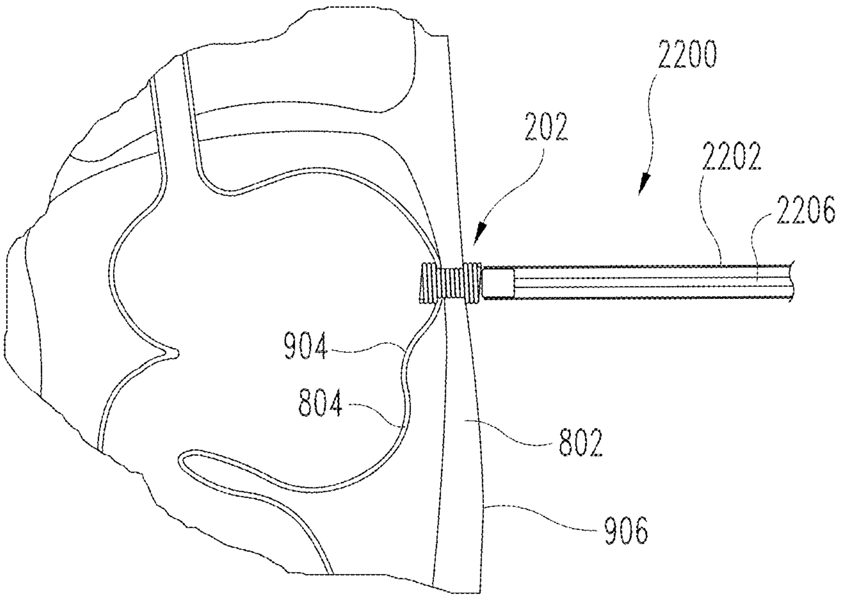

When a distal portion 1704 of the needle has access to the stomach cavity 806, as illustrated in FIG. 17, portions of the device body 202 may be released from the needle 1702 and/or configured from the insertable configuration into the expanded configuration, as illustrated in FIG. 18. For example, the device body 202 may be extended out of the distal portion 1704 of the needle 1702, the needle 1702 may withdrawn from its position over the device body 202, and/or a combination of the two may occur to release the device body 202 from the retention of the delivery device 1700.

The securing device 100 can be made of any material known by one of ordinary skill in the art to be suitable. For example, the device body 202 of the securing device may have portions made of metal. Furthermore, portions of the device body 202 can be self-expanding. For example, the distal portion 204, proximal portion 206, and/or central portion 208 may be self-expandable from the initial configuration into the expanded configuration. A self-expanding portion can include stainless steel, materials with elastic memory properties, such as NITINOL, or any other suitable material, to name a few non-limiting examples.

The needle 1702 and expanded portion of the device body 202 can be withdrawn so as to contact a portion of the expanded portion of the device body 202, such as distal portion 204, with the inner surface 904 of the stomach wall 804 and/or to position the stomach wall 804 into close proximity and/or an adjacent position with the abdominal wall 802. In some instances, the distal tissue surface 214 contacts the inner surface 904 of the stomach wall 804.

Additional portions of the device body 202 can be released from the needle 1702 and/or configured from the insertable configuration into the expanded configuration. For example, a portion of the device body 202 may be released and/or expanded to form the central portion 208 defining the central lumen 338. Additionally, a portion of the device body 202 in the insertable configuration may be released and/or expanded to form the proximal portion 206.

After the device body 202 is released from the delivery device 1700, the abdominal wall 802 and stomach wall 804 of the patient may be held in and/or pressed into close proximity and/or adjacent position with one another by the device body 202. For example, the distal tissue surface 214 of the distal portion 204 can contact the inner surface 904 of the stomach wall 804 and the proximal tissue surface 216 of the proximal portion 206 can contact the outer surface 906 of the abdominal wall 802 to squeeze the abdominal wall 802 and the stomach wall 804 together.

FIGS. 22, 23, 24, and 25 illustrate another device and method that can be used in implanting a securing device, such as the securing device 100. In this embodiment, the delivery device 2200 comprises a tube 2202 having an opening in a distal portion 2204 and containing a pushrod 2206.

Access to the stomach cavity 806 is obtained percutaneously, through the abdominal wall 802 and the stomach wall 804. For example, a needle can be used to make a puncture in the abdominal wall 802 and the stomach wall 804. A wire guide may then be advanced through the needle and/or the puncture into the stomach cavity 806. One or more dilators may be passed over the wire guide to dilate the tract and enlarge the stoma. When the proper size stoma is created, the delivery device 2200 including the tube 2202 may be inserted into the tract.

When an opening in the distal portion 2204 of the tube 2202 has access to the stomach cavity 806, a portion of the device body 202 is released and/or expanded into the expanded configuration. For example, the tube 2202 of the delivery device 2200 may be withdrawn from its position over the device body 202. Alternatively or in addition, the pushrod 2206 may be pressed against a portion of the device body 202 within the tube 2202 so as to force a portion of the device body 202 out of an opening in the distal portion 2204 of the delivery device 2200.

Additional portions of the device body 202 may also be released and/or expanded into their expanded configurations in a similar fashion. For example, a portion of the device body 202 may be expanded to form the central portion 208 having a coiled arrangement defining a central lumen 338 in communication with a distal lumen 234 defined by the distal portion 204. Similarly, a portion of the device body 202 may be expanded to form the proximal portion 206, defining a proximal lumen 236 that is in communication with the central lumen 338 of the central portion 208.

Alternatively, a needle can be used to make a needle puncture in the abdominal wall 802 and the stomach wall 804. A wire guide can then be advanced through the needle and into the stomach. The needle can be removed from the puncture site, leaving the wire guide in place, and one or more dilators may be passed over the wire guide to gradually dilate the stoma and/or tract. When the proper size stoma and/or tract is created, the securing device 100 may be inserted into the stoma with a portion positioned inside of the stomach cavity 806, a portion extending through the stomach wall 804, a portion extending through the abdominal wall 802, and/or a portion positioned outside of the body of the patient.

Kit

The present disclosure also teaches a kit useful for securing an open stoma and/or a percutaneously-implantable tube, such as a percutaneous gastrostomy tube. In some embodiments the kit can comprise a securing device loaded into a delivery device, such as those illustrated above. The kit may also comprise a needle, wire guide, and/or dilators that may be necessary and/or assistive in implanting the securing device in the body of a patient.

In some embodiments, the kit comprises some combination of a securing device with a delivery device; a needle, wire guide, and dilators; a tube, a bag, and/or a plug. For example, the kit may contain a securing device, such as those described above, and a tube that are arranged to cooperate with one another. The securing device can define a lumen having a maximum outer dimension that is substantially the same size as the maximum outer dimension of the tube. Therefore, when the tube is inserted into the lumen defined by the securing device, the securing device retains the tube and resists movement of the tube in one or more directions.

As another example, in some instances the kit comprises a securing device, a tube, and a bag arranged to connect to the tube. In addition, or alternatively, the kit may include a plug arranged to plug one or more lumens defined by the device body of the securing device. Other combinations of the above listed components are also contemplated and will be apparent to one of ordinary skill in the art.

While some embodiments of the invention have been illustrated and described in detail in the drawings and foregoing description, the same is to be considered as illustrative and not restrictive in character, it being understood that a preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A device for securing the wall of an organ to the abdominal wall of a patient, comprising:

a device body having a distal portion, a proximal portion, and a central portion extending between said distal portion and said proximal portion;

said device body configurable between an insertable configuration and an expanded configuration;

said distal portion comprising a first elongate body that in said expanded configuration forms a first coil arrangement having a first maximum outer dimension;

said proximal portion comprising a second elongate body that in said expanded configuration forms a second coil arrangement having a second maximum outer dimension; and said central portion forming a central portion arrangement having a third maximum outer dimension;

wherein said first and said second maximum outer dimensions are greater than said third maximum outer dimension; and wherein said first coil arrangement is self-expanding.

2. The device of claim 1, wherein:

said device body is configured to have said first coil arrangement and said second coil arrangement cooperate to bring a wall of an organ into close proximity with the abdominal wall of a patient.

3. The device of claim 1, wherein:

said device body is longitudinally extendable in said expanded configuration.

4. The device of claim 1, wherein:

said central portion arrangement defines a tissue-free lumen when implanted in the body of a patient.

5. The device of claim 4, wherein:

said tissue-free lumen is arranged to receive a tube.

6. The device of claim 5, wherein:

said tissue-free lumen is arranged to slidably receive the tube, such that the tube is slidably insertable into and slidably removable from within the tissue-free lumen; and wherein an inner surface of said first coil arrangement is arranged to contact and delimit deflection of tube when the tube is slidably received within the tissue-free lumen.

7. The device of claim 1, wherein:

said distal portion comprises a deflectable portion arranged for deflectable movement.

8. The device of claim 1, wherein:

said first elongate body and said second elongate body are portions of an elongate member.

9. The device of claim 1, further comprising:

a biomaterial cover positioned over said central portion.

10. A kit, comprising:

a device for securing a percutaneously-implantable tube, comprising:

a device body having a distal portion, a proximal portion, and a central portion extending between said distal portion and said proximal portion;

said device body configurable between an insertable configuration and an expanded configuration;

said distal portion comprising a first elongate body that in said expanded configuration forms a first coil arrangement having adjacent coils in abutting contact and having a first maximum outer dimension;

said proximal portion comprising a second elongate body that in said expanded configuration forms a second coil arrangement having a second maximum outer dimension; and said central portion forming a central portion arrangement having a third maximum outer dimension;

wherein said first and said second maximum outer dimensions are greater than said third maximum outer dimension; and wherein said proximal portion and said distal portion in said expanded configuration are effective to squeeze the wall of an organ and the abdominal wall of a patient into an adjacent position; and a percutaneously-implantable tube arranged to fit within said central portion and access a location within a body of a patient.

11. The kit of claim 10, wherein:

said first coil arrangement is self-expanding.

12. The kit of claim 10, wherein:

said first elongate body and said second elongate body are portions of an elongate member.

13. The kit of claim 10, wherein:

said device further comprises a biomaterial cover positioned over said central portion.

14. The device of claim 10, wherein:

said distal portion comprises a deflectable portion arranged for deflectable movement.

15. The device of claim 10, wherein:

said device body is longitudinally extendable in said expanded configuration.

16. The kit of claim 10, further comprising:

a bag arranged for communication with said percutaneously-implantable tube.

17. The kit of claim 10, wherein:

said device body is preloaded in a delivery device.

18. The kit of claim 10, further comprising:

a needle and a dilator.

19. The device of claim 10, wherein:

said percutaneously-implantable tube is slidably receivable and removable from said central portion; and wherein an inner surface of said first coil arrangement is arranged to contact and delimit deflection of the percutaneously-implantable tube when the tube is slidably received within the central portion.

20. A device for securing the wall of an organ to the abdominal wall of a patient, comprising:

a wire having a distal portion, a proximal portion, and a central portion extending between said distal portion and said proximal portion;

said wire configurable between an insertable configuration and an expanded configuration;

said distal portion comprising a first securing portion that in said expanded configuration forms a first coil arrangement having a first maximum outer dimension;

said proximal portion comprising a second securing portion that in said expanded configuration forms a second coil arrangement having a second maximum outer dimension; and said central portion forming a third coil arrangement having a third maximum outer dimension;

wherein said first and said second maximum outer dimensions are greater than said third maximum outer dimension; and wherein said wire terminates with a free end at said distal portion.

* * * * *